United States Patent [19]
Shahid

[11] Patent Number: 6,025,515
[45] Date of Patent: *Feb. 15, 2000

[54] USE OF SUBSTITUTED PHENOLS TO INHIBIT POLYMER FORMATION DURING THE MANUFACTURE OF ACRYLONITRILE

[75] Inventor: Muslim D. Shahid, Houston, Tex.

[73] Assignee: Baker Hughes Incorporated, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/755,891

[22] Filed: Sep. 23, 1996

Related U.S. Application Data

[63] Continuation of application No. 08/485,173, Jun. 7, 1995, abandoned.

[51] Int. Cl.[7] .................................................. C07C 255/00
[52] U.S. Cl. ........................ 558/305; 558/306; 558/462; 558/466; 526/82; 526/212; 526/341
[58] Field of Search ............................ 526/212, 82, 341; 558/466, 305, 306, 462

[56] References Cited

U.S. PATENT DOCUMENTS

| | | | |
|---|---|---|---|
| 3,689,558 | 9/1972 | Modeen et al. | 564/127 |
| 3,821,177 | 6/1974 | Chan . | |
| 3,915,941 | 10/1975 | Chan . | |
| 3,946,066 | 3/1976 | Todd | 558/364 |
| 4,017,544 | 4/1977 | Mullins . | |
| 4,701,546 | 10/1987 | Bewert et al. | 558/445 |
| 4,720,566 | 1/1988 | Martin | 558/306 |
| 5,128,484 | 7/1992 | Kita et al. | 548/549 |
| 5,288,473 | 2/1994 | Shaw et al. . | |

*Primary Examiner*—Bernard Lipman
*Attorney, Agent, or Firm*—Madan & Morris, P.C.

[57] ABSTRACT

The present invention provides substituted phenols which are effective to inhibit polymer formation during the manufacture of acrylonitrile. Preferred substituted phenols are (a) hindered phenols, nonhindered phenols, and partially hindered phenols, or (b) combinations of hindered phenols with nonhindered or partially hindered phenols. A most preferred substituted phenol is p-nitrosophenol. In a preferred embodiment, the substituted phenols (with the exception of p-nitrosophenol) are combined with hydrogen transfer agents.

12 Claims, 1 Drawing Sheet

USE OF SUBSTITUTED PHENOLS TO INHIBIT POLYMER FORMATION DURING THE MANUFACTURE OF ACRYLONITRILE

This is a continuation-in-part of application Ser. No. 08/485,173, filed Jun. 7, 1995 abandoned.

FIELD OF THE INVENTION

The present invention relates to substituted phenols, preferably combined with hydrogen transfer agents, which are effective to inhibit polymer formation during the manufacture of acrylonitrile. Preferred substituted phenols are (a) hindered phenols, nonhindered phenols, and partially hindered phenols, or (b) combinations of hindered phenols with nonhindered or partially hindered phenols. A most preferred substituted phenol is p-nitrosophenol.

BACKGROUND OF THE INVENTION

Acrylonitrile is produced commercially in systems using what is known as the "Sohio" process, described in U.S. Pat. No. 2,904,580 to Idol. The reactor feeds in a commercial acrylonitrile system using the, "Sohio" process are propylene, ammonia, and compressed air. The propylene and ammonia are vaporized, combined with the air, and fed to a fluidized bed catalytic reactor. Precise ratios of the three feeds are maintained for optimum yield.

The manufacture of acrylonitrile has four basic stages: a reaction stage, in which the ammonia and propylene are reacted; a cooling stage, in which the reaction product is cooled; an absorption stage, in which a crude acrylonitrile product is collected; and, a purification stage, in which the crude acrylonitrile product is purified.

In the reaction stage, the propylene, ammonia, and compressed air feeds are mixed together in a reactor and react on the surface of a fluidized catalyst. A set of complex exothermic reactions takes place, forming the following products: acrylonitrlle, hydrogen cyanide, carbon dioxide, carbon monoxide, acetonitrile, hydrogen acrolein, acrylic acid, water, other higher nitrltes, aldehydes, ketones, acetic acid, and a number of miscellaneous unknown organic compounds. Conversion of the three feeds is less than 100%; therefore, unreacted propylene, ammonia, oxygen, and nitrogen are contained in the reactor effluent gas.

A portion of the heat produced by the exothermic reaction is removed by sets of steam coils. Reactor effluent gas passes through cyclones, which remove catalyst fines from the gas. The gas then is cooled in a reactor effluent cooler comprised of a shell and a tube exchanger using boiler feedwater as the cooling source.

In the cooling stage, the gas leaving the reactor effluent cooler is cooled in a quench column by contact with a recirculating water stream. Most of the water vapor and small amounts of organic vapors in the gas are condensed in the quench column. The quench column bottoms are cooled and circulated back to the quench column. The excess quench water is roughly equal to the amount of water produced by the reactor and is fed to the wastewater column, where acrylonitrile and hydrogen cyanide are recovered. Wastewater column bottoms ultimately are injected into the wastewater injection well.

In the absorption stage, the quench column effluent gas is directed to an absorber where chilled water is used to absorb acrylonitrile, hydrogen cyanide, and other organics from the gas. Absorber bottoms are fed to a recovery column where a crude acrylonitrile product is taken overhead.

The crude acrylonitrile product then goes through a purification stage in a series of distillation columns. The first column (heads column) removes hydrogen cyanide, while the second column (drying column) removes water. The last column (product column) takes pure acrylonitrile monomer from a side-draw near the top of the column. Heavy ends are rejected from the product column bottoms.

Unfortunately, the acrylonitrile monomer can polymerize during the cooling stage in the quench column and during the purification stage in the distillation columns. The acrylonitrile that does polymerize in the quench column and/or distillation columns represents an undesirable net product loss for the acrylonitrile plant.

Inexpensive compounds that effectively inhibit the premature polymerization of acrylonitrile during its manufacture are sorely needed.

SUMMARY OF THE INVENTION

The present invention provides substituted phenols which are effective to inhibit polymer formation during the manufacture of acrylonitrile. Preferred substituted phenols are (a) hindered phenols, nonhindered phenols, and partially hindered phenols, or (b) combinations of hindered phenols with nonhindered or partially hindered phenols. A most preferred substituted phenol is p-nitrosophenol. In a preferred embodiment, the substituted phenols (with the exception of p-nitrosophenol) are combined with hydrogen transfer agents.

DETAILED DESCRIPTION OF THE INVENTION

Figure 1:
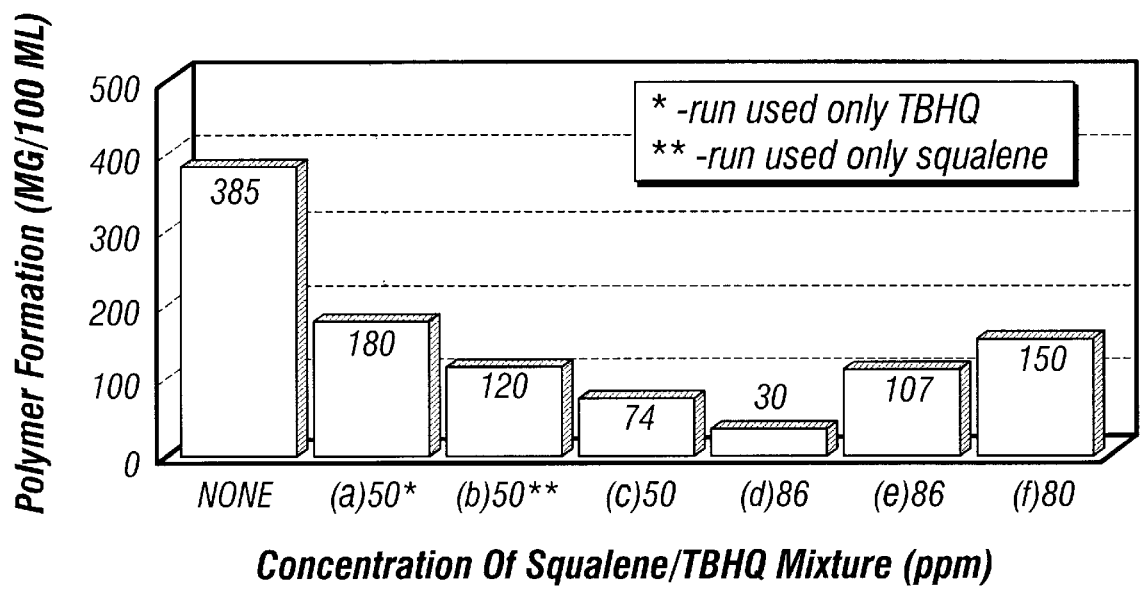
FIG. 1 is a chart showing the inhibition of acrylonitrile polymerization achieved using varying amounts of TBHQ, squalene, and MEHQ, as described in Example 5.

The substituted phenols of the present invention include "nonhindered phenols" or "partially hindered phenols," which are defined as having the following formula:

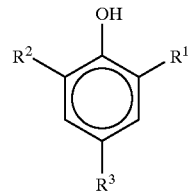

wherein $R^1$ and $R^2$ are selected from the group consisting of hydrogen, hydroxyl groups, alkyl groups, including cyclic and heterocyclic alkyl groups, aryl groups, alkaryl groups, and aralkyl groups, provided that, if $R^1$ is a hydroxyl group, an alkyl group, an aryl group, an alkaryl group, or an aralkyl group, then $R^2$ must be hydrogen; and $R^3$ is selected from the group consisting of alkyl groups, including cyclic and heterocyclic alkyl groups, aryl groups, alkaryl groups, aralkyl groups, alkyloxy groups, substituted or unsubstituted amino groups, and nitroso groups. The size of the substituents are limited only insofar as steric hindrance may interfere with the efficiency of the molecule as an inhibiting agent. In a preferred embodiment, the alkyl groups have between about 1–9 carbon atoms.

The term "nonhindered phenols" or "partially hindered phenols" also is intended to include compounds having the following structure:

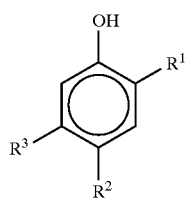

wherein $R^1$, $R^2$, and $R^3$ are selected from the group consisting of hydrogen, hydroxyl groups, alkyl groups, including cyclic and heterocyclic alkyl groups, aryl groups, alkaryl groups, and aralkyl groups, wherein $R^2$ and $R^3$ may be joined together to form cyclic and heterocyclic alkyl groups. The size of the substituents are limited only insofar as steric hindrance may interfere with the efficiency of the molecule as an inhibiting agent. Compounds having the foregoing structure may be purchased or manufactured as shown in Pospisil J., Kotulak, L., Taimr, L. *Europ. Poly. J.* 7 (1971) 255; Taimr, L., Pospisil, *J. Tetrahedron Letters* (1961) 4, 5, and 6, both of which are incorporated herein by reference.

In a preferred embodiment, $R^2$ and $R^3$ are joined together to form 3,3,3',3'-tetramethyl-1,1'-spirobisindane-5,5',6,6'-tetrol, which has the following structure, and is available from Eastman Chemicals:

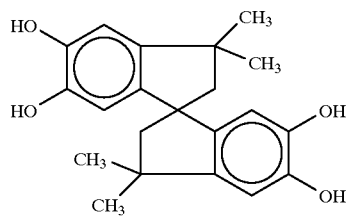

Preferred non-hindered and partially hindered phenols include, but are not necessarily limited to: p-nitrosophenol (PNP), which is available from Sandoz Chemicals, and which also may be manufactured as described in Example 1; 3,3,3',3'-tetramethyl-1,1'-spirobisindane-5,5',6,6'-tetrol; butylated hydroxyanisole (BHA), which is available from Eastman Chemicals; monomethyl ether hydroquinone (MEHO), which is available from Eastman Chemicals; 2,4-di-tert-butyl phenol, which is available from Ethyl Corp.; hydroquinone (HP), which is available from Eastman Chemicals; tert-butyl hydroquinone (TBHQ), which is available from Eastman Chemicals; 4-tert-butyl catechol (TBC), which is available from Janssen Chimica; and, cresol, which is available from Metrichem Corp.

The substituted phenols of the present invention also include "hindered phenols," which are defined as having the formula:

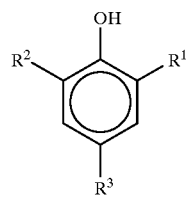

wherein $R^1$ and $R^2$ independently are selected from the group consisting of alkyl groups, including cyclic and heterocyclic alkyl groups, aryl groups, alkaryl groups, and aralkyl groups; and, wherein $R^3$ is selected from the group consisting of hydrogen, alkyl groups, including cyclic and heterocyclic alkyl groups, aryl groups, alkaryl groups, aralkyl groups, alkyloxy groups, and substituted or unsubstituted amino groups. The size of the substituents are limited only insofar as steric hindrance may interfere with the efficiency of the molecule as an inhibiting agent. In a preferred embodiment, the alkyl groups have between about 1–9 carbon atoms.

Preferred hindered phenols include, but are not necessarily limited to: 2,6-di-tert-butyl-4-methyl-phenol (BHT), which is available from Universal Oil Products; 2,6-di-tert-butyl phenol, which is available from Ethyl Corp.; 2,6-dimethyl phenol, which is available from Metrichem Corp.; 2,4,6-tri-tert butyl phenol, which is available from Aldrich; 2,6-di-tert-butyl-4-amine phenol, which is available from Aldrich; and, 2,4-di-tert-butyl phenol.

The substituted phenol(s) can be added to the acrylonitrile reaction mixture, together or separately, using any conventional method, preferably using a suitable carrier solvent which is compatible with the acrylonitrile reaction solution or vapor. Suitable carrier solvents include, but are not necessarily limited to: hydrocarbons and heavy aromatic napthas; xylenes; toluenes; kerosine; mineral oils and acetone; alcohols, such as octanol, hexanol, and 1,4-butanediol; and, aprotic solvents, such as dimethylformamide, dimethylsulfoxide (DMSO), pyrrolidone, and N-methyl pyrrolidone.

Preferably, the substituted phenol is injected into the reactor effluent gas downstream of the reactor effluent cooler, most preferably during the purification stage. The total amount of substituted phenol that is required to inhibit polymerization of acrylonitrile will vary according to the particular conditions of use. At higher temperatures, larger amounts of substituted phenol generally will be required to inhibit polymerization. In a preferred embodiment, para-nitrosophenol is added at between about 10–500 ppm, preferably between about 15–60 ppm, based upon the weight of the acrylonitrile. A preferred total amount of hindered, partially hindered, and/or non-hindered phenol is between about 20–70 ppm based upon the weight of the acrylonitrile, preferably between about 20–45 ppm, most preferably about 26 ppm.

In a preferred embodiment, the substituted phenols of the present invention are added to the reaction mixture in conjunction with a hydrogen transfer agent. Suitable hydrogen transfer agents include compounds comprised of aromatic and aliphatic rings fused together. The aliphatic moiety in such molecules naturally tends to convert to an aromatic moeity, which facilitates the transfer of hydrogen. Examples of such hydrogen transfer agents include, but are not necessarily limited to: 9,10-dihydroanthracene, available from Aldrich; tetralin, available from Dupont Chemicals; fluorene, available from Carbochem USA; naphthalene, available from Carbochem USA; anthracene, available from Carbochem USA; decalin, available from Dupont Chemicals; tetrahydroquinoline, available from Chugai Boyeki (America) Corp.; and, similar compounds.

Other suitable hydrogen transfer agents are isoprenoids, such as squalane and squalene, available from Chugai Boyeki (America) Corp. Preferred hydrogen transfer agents include, but are not necessarily limited to squalene and tetralin.

A preferred inhibiting agent is para-nitrosophenol. Para-nitrosophenol is such an efficient inhibiting agent that it preferably is used alone; however, para-nitrosophenol may be used with a hydrogen transfer agent.

Another preferred embodiment includes a hydrogen transfer agent combined with a hindered phenol and a non-hindered or partially hindered phenol. A preferred example of this embodiment is squalene, as the hydrogen transfer agent, and a combination of tert-butyl hydroquinone (TBHQ) with monomethyl ether hydroquinone (MEHO). A preferred molar ratio for this embodiment is 2.5:4.3:4.3:: MEHQ:TBHQ:squalene.

Another preferred example of this embodiment is tetralin, as the hydrogen transfer agent, and a combination of 2,6-di-tert-butyl-4-methyl-phenol (BHT) and monomethyl ether hydroquinone (MEHO). A preferred molar ratio for this embodiment is 2.5:6.5:2.5:: MEHQ:BHT:tetralin.

Given the foregoing basic materials, persons of skill in the art will be able to develop other optimal combinations of hydrogen transfer agents and substituted phenols to achieve similar levels of inhibition.

The invention will be better understood with reference to the following examples:

EXAMPLE 1

Paranitrosophenol is prepared using the following procedures. 98.0 g (1.42 moles) of $NaNO_2$ are charged to a 1 L 5-neck round bottom flask and dissolved in 400 mL of water. The contents are cooled to 0° C. with a salt/ice bath. While the contents are cooling, two solutions are prepared separately.

Solution A is prepared by dissolving 94.0 g (1.00 mole) of phenol in 20.0 g of acetic acid with mild heating. The resulting solution is charged to an addition funnel.

Solution B is prepared by dissolving 60.0 g of 96% $H_2SO_4$ in 60 mL of $H_2O$. The resulting solution is charged to an addition funnel.

After adding 10.0 g of acetic acid to the round bottom flask, solutions A and B are added to the flask concurrently at a rate that permits the reaction temperature not to exceed 5° C. The PNP precipitates during the reaction, and vigorous stirring is maintained at all times. After both solutions are completely added, the flask contents are warmed to ambient temperature in tepid water while continuing to stir for at least ½ hour. The contents of the flask are then vacuum filtered and washed with 600 mL of water. The solid brown precipitate, which contains the paranitrosophenol, is then collected.

EXAMPLE 2

The materials shown below, in Table I, were screened using the following procedures.

100 ml of acrylonitrile monomer obtained from Sterling Chemical Co., Texas City, Texas was charged to a 250 ml three-neck round bottom flask. The desired amount of inhibitor and/or other material (gen., 50 ppm) was added to the acrylonitrile monomer. 200 ppm of the initiator tert-butyl hydroperoxide was added to the acrylonitrile or acrylonitrile/inhibitor solution to (a) decrease the time required for any polymerization to occur, and (b) to more closely simulate the expected environment in actual use. With the condenser attached to the reaction vessel, the monomer material was heated and refluxed for four and one-half hours. The stressed acrylonitrile was cooled to 32° C. (90° F.), and 100 ml of n-heptane was added. The white polymer material was allowed to precipitate out of solution for 30 minutes. The liquid/polymer material then was filtered through a FisherBrand glass fiber filter paper (G6), diameter 7.00 cm (cat. No. 09-804-70A), using a Buchner funnel with vacuum. The filter paper was placed in a pre-weighed Petri-dish and dried in a vacuum oven (27–30 mmHg) at 107° C. (225° F.) for 1 hour. The Petri-dish was removed from the oven, placed in a desiccator, and cooled under vacuum (27–30 mmHg) for 1 hour. The weight of any polymer formed was determined and recorded. The results also are given in Table I.

TABLE I

| Additive | (ppm active) | (wt. polymer (mg)) | |
|---|---|---|---|
| none | — | 414 | |
| " | " | 366 | |
| " | " | 436 | |
| " | " | 332 | |
| " | " | 349 | |
| " | " | 369 | |
| " | " | 358 | |
| " | " | 404 | |
| " | " | 367 | |
| t-butyl Hydroquinone | 50 | 191 | 50% |
| NAUGARD 529, polymerized alkylated phenol, Uniroyal Chemical Co. | 50 | 336 | 11% |
| TENOX BHA, butylated hydroxy anisole, Eastman Kodak | 50 | 162 | 57% |
| ETHANOX 330, 1,3,5-trimethyl-2,4,6-tris(3,5-di-t-butyl-4-hydroxybenzyl) butane, Ethyl Corp. | 50 | 299 | 21% |
| BHT | 50 | 192 | 49% |
| IRGANOX 1076, octadecyl-3-3,5-di-t-butyl-4-hydroxyphenylpropionate, Ciba Giegy | 50 | 219 | 42% |
| IRGANOX 1010, tetrakis [methylene-3-(3,5-di-t-butyl-4-hydroxyphenyl) propionate] methane, Ciba Geigy | 50 | 276 | 27% |
| TBC t-butyl-pyrocatechol, Aldrich | 50 | 180 | 5% |
| 2,4,6-tri-t-butylphenol, Janssen Chemicals | 50 | 241 | 36% |
| P-Nitrosophenol, Sandoz Chemical Co. | 83 | 0 | 100% |
| MEHQ, Eastman Kodak | 50 | 216 | 43% |
| P-Nitrosophenol (in a 7% KOH soln.) | 50 | 0 | 100% |

The materials that exhibited some level of inhibition were subjected to further testing. Materials exhibiting 100 mg of polymer or less are preferred.

EXAMPLE 3

The materials shown below in Table II were screened using the procedures given in Example 2. All runs contained 25 ppm MEHQ. The results are given in Table II.

TABLE II

| Additive | (ppm active) | [wt. polymer (mg)] |
|---|---|---|
| none | — | 348 |
| BHT/Squalene | 25/25 | 100 |
| BHA/Squalane | 25/25 | 191 |
| TBHQ/Squalane | 25/25 | 130 |
| BHT/Squalane | 25/25 | 191 |
| TBHQ/Squalene | 25/25 | 74 |
| BHT/Tetralin | 25/25 | 178 |
| TBHQ/Tetralin | 25/25 | 158 |
| none | — | 833 |
| none | — | 899 |
| Squalene/TBHQ | 61/25 | 30 |
| TBHQ/Squalene | 61/25 | 107 |
| Squalene/TBHQ | 40/40 | 150 |
| none | — | 382 |
| BHT/Tetralin | 42/25 | 98 |
| TBHQ/Tetralin | 35/25 | 120 |
| BHT/Tetralin | 54.5/25 | 74 |
| BHT/Tetralin | 59/35 | 171 |
| BHT/Tetralin | 65/25 | 11 |
| PNP (15% KOH) | 50 | 0 |
| BHT/Tetralin | 81/25 | 169 |
| BHT | 81 | 116 |
| Tetrahydroquinoline | 50 | 320 |
| BHT | 25 | 200 |
| BHT | 65 | 187 |

The materials exhibiting some inhibition were subjected to further testing. Materials exhibiting 100 mg of polymer or less are preferred.

EXAMPLE 4

The materials shown in Table III were subjected to the following procedures.

100 ml of acrylonitrile monomer obtained from Sterling Chemical Co., Texas City, Texas was charged to a 250 ml three-neck round bottom flask. The indicated amount of inhibitor and any other desired material (ppm) was added to the acrylonitrile monomer. 200 ppm of the initiator tert-butyl hydroperoxide was added to the acrylonitrile or acrylonitrile/inhibitor solution.

The system was purged with nitrogen for 18 minutes, allowing all nitrogen/air to be removed through the open end of the reflux condenser. While continuing to purge, the contents of the flasks were heated to reflux 70–75° C. (158–163° F.) and held for three hours. The solution was cooled to 32° C. (90° F.) under nitrogen atmosphere. The nitrogen addition was stopped, and 100 ml of n-heptane was added.

The white polymer material was allowed to precipitate out of solution for 30 minutes. The liquid/polymer material then was filtered through a FisherBrand glass fiber filter paper (G6), diameter 7.00 cm (cat. No. 09-804-70A), using a Buchner funnel with vacuum. The filter paper was placed in a pre-weighed Petri-dish and dried in a vacuum oven (27–30 mHg) at 107° C. (225° F.) for 1 hour. The Petri-dish was removed from the oven, placed in a desiccator, and cooled under vacuum (27–30 mmHg) for 1 hour. The weight of any polymer formed was determined and recorded. The proportions of materials and the results are reflected in Table III:

TABLE III

| Additive | (ppm active) | (wt. polymer (mg) |
|---|---|---|
| none | — | 760 (fresh) |
| PNP | 25 | 0 |
| PNP | 25 | 0 |
| BHT | 33 | 644 |
| BHT/Tetralin | 33/13 | 656 |
| none | — | 1,244 (4 day old) |
| BHT/Tetralin/MEHQ | 33/13/10 | 585 |
| TST, tetramethyl-spirobisindane, Aldrich | 9 | 474 |
| BHT/Tetralin/MEHQ | 130/50/10 | 148 |
| BHT/Tetralin | 130/50 | 249 |
| none | — | 722 (fresh) |
| BHT/Tetralin/MEHQ | 130/25/10 | 143 |
| BHT/Tetralin/MEHQ | 130/50/10 | 300 (old tet) |
| none | — | 1,000 (4 day old) |
| BHT/Tetralin/MEHQ | 80/25/10 | 182 |
| BHT/Tetralin/TBHQ | 80/25/10 | 236 |
| BHT/Tetralin/MEHQ | 55/25/25 | 114 |
| TST/Tetralin/MEHQ | 55/25/25 | 0 |
| BHT/Tetralin/TBHQ | 55/25/25 | 234 |
| none | — | 1,000 (3 day old) |
| 4,6-di-tert-butyl-2-methylphenol*/MEHQ/tetralin | 55/25/25 | 469 |
| TST/tetralin | 55/25 | 250 |
| BHT/TST/Tetralin | 50/35/15 | 24 |
| BHT/Tetralin/MEHQ | 50/35/15 | 247 |
| Squalene/TST/MEHQ | 50/35/15 | 120 |

*The 4,6-di-tert-butyl-2-methylphenol was obtained from Schenectady Chemical Co.

EXAMPLE 5

100 ml of acrylonitrile monomer obtained from Sterling Chemical Co., Texas City, Tex. was charged to seven 250 ml three-neck round bottom flasks. 25 ppm of MEHO was added to each flask along with the following:

| FLASK | MATERIALS ADDED |
|---|---|
| (a) | 50 ppm TBHQ |
| (b) | 50 ppm squalene |
| (c) | 25 ppm TBHQ; 25 ppm squalene (molar ratio, 0.4) |
| (d) | 25 ppm TBHQ; 61 ppm squalene (molar ratio, 1:1) |
| (e) | 61 ppm TBHQ; 25 ppm squalene (molar ratio, 1.9) |
| (f) | 40 ppm TBHQ; 40 ppm squalene (molar ratio, 0.4). |

200 ppm of the tert-butyl hydroperoxide was added to the acrylonitrile or acrylonitrile/inhibitor solution. With the condenser attached to the reaction vessels, the monomer material was heated and refluxed for four and one-half hours. The stressed acrylonitrile was cooled to 32° C. (90°)F., and 100 ml of n-heptane was added. The white polymer material was allowed to precipitate out of solution for 30 minutes.

The liquid/polymer material was filtered through a FisherBrand glass fiber filter paper (G6), diameter 7.00 cm (cat. No. 09-804-70A), using a Buchner funnel with vacuum. The filter paper was placed in a pre-weighed Petri-dish and dried in a vacuum oven (27–30 mmHg) at 107° C. (225° F.) for 1 hour. The Petri-dish was removed from the oven, placed in a desiccator, and cooled under vacuum (27–30 mmHg) for 1 hour. The weight of any polymer formed was determined and recorded. The results are shown in FIG. 1.

FIG. 1 demonstrates that the optimum treatment was 25 ppm of MEHQ and 86 ppm of a 1:1 ratio of squalene:TBHQ.

EXAMPLE 6

Figure 2:
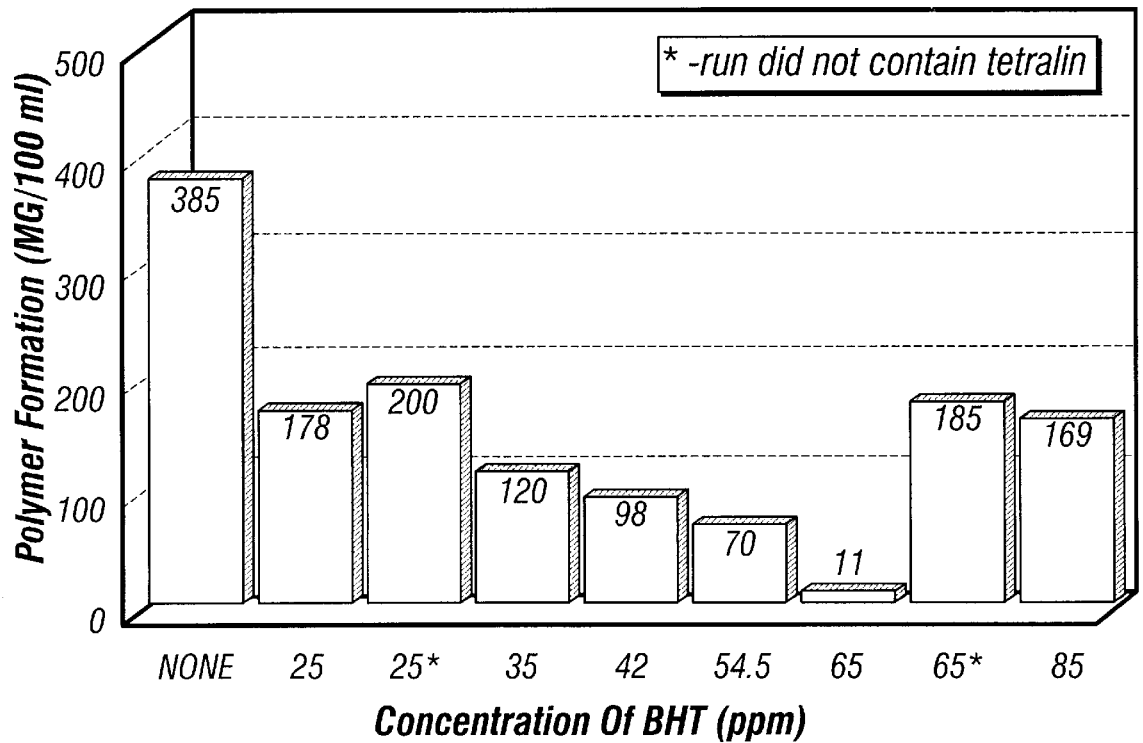
FIG. 2 is a chart showing the inhibition of acrylonitrile polymerization achieved using varying amounts of BHT, tetralin, and MEHQ, as described in Example 6.

The procedures of Example 5 were followed using 25 ppm MEHQ and various levels of BHT, with and without 25 ppm of tetralin as a hydrogen transfer agent. The results are given in FIG. 2. FIG. 2 demonstrates that optimum results were obtained at 65 ppm of BHT.

Persons of skill in the art will appreciate that many modifications may be made to the embodiments described herein without departing from the spirit of the present invention. Accordingly, the embodiments described herein are illustrative only and are not intended to limit the scope of the present invention.

I claim:

1. A method for treating a reaction mixture for the manufacture of acrylonitrile monomers, said reaction mixture comprising a combination of materials selected from the group consisting of propylene, ammonia, acrylonitrile monomer, byproducts from manufacture of said acrylonitrile monomers, and a catalyst effective to catalyze conversion of said propylene and said ammonia to said acrylonitrile monomer, said method comprising adding a substituted phenol to said reaction mixture in an amount sufficient to inhibit polymerization of said acrylonitrile monomer under conditions of manufacture of said acrylonitrile monomer, wherein said substituted phenol is selected from the group consisting of 3,3,3',3'-tetramethyl-1,1'-spirobisindane-5,5',6,6'-tetrol; 2,6-di-tert-butyl phenol; 2,6-di-tert-butyl-4-methyl-phenol; 2,6-di-methyl phenol; 2,4,6-tri-tert butyl phenol; 2,6-di-tert-butyl-4-amine phenol; and, 2,4-di-tert-butyl phenol.

2. A method for treating a reaction mixture for the manufacture of acrylonitrile monomers, said reaction mixture comprising a combination of materials selected from the group consisting of propylene, ammonia acrylonitrile monomer, byproducts from manufacture of said acrylonitrile monomers, and a catalyst effective to catalyze conversion of said propylene and said ammonia to said acrylonitrile monomer, said method comprising adding a substituted phenol to said reaction mixture in an amount sufficient to inhibit polymerization of said acrylonitrile monomer under conditions of manufacture of said acrylonitrile monomer, wherein said substituted phenol is selected from the group consisting of p-nitrosophenol; butylated hydroxyanisole; monomethyl ether hydroquinone; 2,4-di-tert-butyl phenol; hydroguinoneo tert-butyl hydroquinone; 4-tert-butyl catechol; cresol; 3,3,3',3'-tetramethyl-1,1'-spirobisindane-5,5',6,6'-tetrol; 2,6-di-tert-butyl phenol; 2,6-di-tert-butyl-4-methyl-phenol; 2,6-di-methyl phenol; 2,4,6-tri-tert butyl phenol; 2,6-di-tert-butyl-4-amine phenol; and, 2,4-di-tert-butyl phenol.

3. A method for treating a reaction mixture for the manufacture of acrylonitrile monomers, said reaction mixture comprising a combination of materials selected from the group consisting of propylene, ammonia acrylonitrile monomer, byproducts from manufacture of said acrylonitrile monomers, and a catalyst effective to catalyze conversion of said propylene and said ammonia to said acrylonitrile monomer said method comprising adding a substituted phenol to said reaction mixture in an amount sufficient to inhibit polymerization of said acrylonitrile monomer under conditions of manufacture of said acrylonitrile monomer; and adding a hydrogen transfer agent to said reaction mixture.

4. A method for treating a reaction mixture for the manufacture of acrylonitrile monomers, said reaction mixture comprising a combination of materials selected from the group consisting of propylene, ammonia, acrylonitrile monomer, byproducts from manufacture of said acrylonitrile monomers, and a catalyst effective to catalyze conversion of said propylene and said ammonia to said acrylonitrile monomer, said method comprising adding to said reaction mixture a substituted phenol selected from the group consisting of hindered phenols, non-hindered phenols, partially hindered phenols, and combinations thereof, in an amount sufficient to inhibit polymerization of said acrylonitrile monomer under conditions of manufacture of said acrylonitrile monomer, said methods; and adding a hydrogen transfer agent to said reaction mixture.

5. The method of claim 2 further comprising the step of adding a hydrogen transfer agent to said reaction mixture.

6. The method of claim 3 wherein said hydrogen transfer agent is selected from the group consisting of squalane; squalene; 9,10-dihydroanthracene; tetralin; fluorene; naphthalene; anthracene; decalin; and, tetrahydroquinoline.

7. The method of claim 4 wherein said hydrogen transfer agent is selected from the group consisting of squalane; squalene; 9,10-dihydroanthracene; tetralin; fluorene; naphthalene; anthracene; decalin and, tetrahydroquinoline.

8. The method of claim 5 wherein said hydrogen transfer agent is selected from the group consisting of squalane; squalene; 9,10-dihydroanthracene; tetralin; fluorene; naphthalene; anthracene; decalin; and, tetrahydroquinoline.

9. The method of claim 8 wherein said hydrogen transfer agent is squalene;

said substituted phenol comprises a combination of tert-butyl hyroquinone and monomethyl ether hydroquinone; and said hydrogen transfer agent and said substituted phenol are added at a molar ratio of about 2.5:4.3:4.3:: squalene:t-butyl hydroquinone:monomethyl ether hydroquinone.

10. The method of claim 8 wherein said hydrogen transfer agent is tetralin; and said substituted phenol comprises a combination of 2,6-di-tert-butyl-4-methyl-phenol and monomethyl ether hydroquinone; and, said hydrogen transfer agent and said substituted phenol are added at a molar ratio of about 2.5:6.5:2.5:: monoethyl ether hydroquinone;2,5-tert-butyl-4-methyl-phenol;tetralin.

11. A reaction mixture for manufacturing acrylonitrile comprising compounds selected from the group consisting of acrylonitrile and precursors thereof; and, a substituted phenol selected from the group consisting of hindered phenols, non-hindered phenols, partially hindered phenols, and combinations thereof, wherein said substituted phenol inhibits polymerization of acrylonitrile at temperatures of up to at least about 94° C. (200° F.) in the presence and in the absence of oxygen, and wherein said substituted phenol is present in an amount sufficient to inhibit said polymerization of said acrylonitrile but insufficient to initiate polymerization of said acrylonitrile;

wherein said non-hindered and partially hindered phenols are selected from the group consisting of p-nitrosophenol; butylated hydroxyanisole; monomethyl ether hydroquinone; 2,4-di-tert-butyl phenol; hydroquinone; tert-butyl hydroquinonew 4-tert-butyl catechol; and, cresol;

wherein said hindered phenols are selected from the group consisting of 3,3,3', 3'-tetramethyl-1,1'-spirobisindane-5,5', 6,6'-tetrol; 2,6-di-tert-butyl phenol; 2,6-di-tert-butyl-4-methyl-phenol; 2–6-di-methyl phenol; 2–4–6-tri-tert butyl phenol; 2–6-di-tert-butyl-4-amine phenol; and, 2–4-di-tert-butyl phenol; and wherein said reaction mixture further comprises a hydrogen transfer agent.

12. The reaction mixture of claim 11 wherein said hydrogen transfer agent is selected from the group consisting of squalane; squalene; 9,10-dihydroanthracene; tetralin; fluorene; naphthalene; anthracene; decalin, tetrahydroquinoline.

* * * * *